United States Patent [19]

Narayanan et al.

[11] Patent Number: 5,283,229

[45] Date of Patent: * Feb. 1, 1994

[54] DELIVERY SYSTEM FOR AGRICULTURAL CHEMICALS

[75] Inventors: Kolazi S. Narayanan, Palisades; Ratan K. Chaudhuri, Butler, both of N.J.

[73] Assignee: ISP Investments Inc., Wilmington, Del.

[*] Notice: The portion of the term of this patent subsequent to Dec. 10, 2008 has been disclaimed.

[21] Appl. No.: 726,101

[22] Filed: Jul. 5, 1991

Related U.S. Application Data

[63] Continuation-in-part of Ser. No. 654,250, Feb. 12, 1991, which is a continuation-in-part of Ser. No. 546,014, Jun. 28, 1990, Pat. No. 5,156,666, which is a continuation-in-part of Ser. No. 505,030, Apr. 5, 1990, Pat. No. 5,160,528, which is a continuation-in-part of Ser. No. 448,707, Dec. 11, 1989, Pat. No. 5,071,463.

[51] Int. Cl.$^5$ .............................................. A01N 25/30
[52] U.S. Cl. ................................ 504/116; 71/DIG. 1; 424/405
[58] Field of Search ............... 71/121, 103, DIG. 1, 71/118; 504/116; 424/405; A01N 25/30

[56] References Cited

U.S. PATENT DOCUMENTS

| | | | |
|---|---|---|---|
| 3,342,673 | 9/1967 | Kaufman et al. | 514/443 |
| 4,500,343 | 2/1985 | Burow, Jr. | 71/88 |
| 5,071,463 | 12/1991 | Narayanan et al. | 71/79 |
| 5,156,666 | 10/1992 | Narayanan et al. | 504/116 |

*Primary Examiner*—Richard L. Raymond
*Assistant Examiner*—S. Mark Clardy
*Attorney, Agent, or Firm*—Jules E. Goldberg; Marilyn J. Maue; Joshua J. Ward

[57] ABSTRACT

An emulsifiable concentrate of agriculturally active chemical which, upon dilution, produces a highly stable emulsion and avoids precipitation of the active ingredient on extended storage. The inventive concentrate is composed of an agriculturally active chemical, a surfactant, and a solvent composed of first and second components. The first component has a hydrophilic property sufficiently high so as to solubilize the agriculturally active chemical. The second component is a hydrophobic solvent and is composed of at least between about 5 to 90 percent by weight of a compound having the structure:

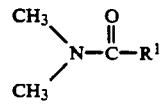

wherein $R^1$ is an alkyl having from 5 to 18 carbon atoms.

47 Claims, 1 Drawing Sheet

DELIVERY SYSTEM FOR AGRICULTURAL CHEMICALS

CROSS-REFERENCE TO OTHER APPLICATIONS

This application is a continuation-in-part of co-pending application Ser. No. 07/654,250, filed Feb. 12, 1991, which, in turn, is a continuation-in-part of application Ser. No. 07/546,014, filed Jun. 28, 1990, now U.S. Pat. No. 5,156,666, which, in turn, is a continuation-in-part of application Ser. No. 505,030, filed Apr. 5, 1990, now U.S. Pat. No. 5,160,528, which, in turn, is a continuation-in-part of application Ser. No. 07/448,707, filed Dec. 11, 1989, now U.S. Pat. No. 5,071,463.

BACKGROUND OF THE INVENTION

I. Field of the Invention

The invention relates to a delivery system for agriculturally active chemicals. More particularly, the invention relates to an emulsifiable concentrate of difficult to dissolve agricultural chemicals making use of biodegradable solvents.

II. Description of the Prior Art

Agricultural chemicals are most preferably applied in the form of aqueous emulsions, solutions, or suspensions. Occasionally, they may also be applied in the form of a dust wherein the active ingredient is adsorbed onto or mixed with a finely divided inert carrier material, such as, china clay, or the like. With such powdered or dust compositions, drift due to wind is a problem and consequently, liquid formulations are preferred.

One of the problems with such liquid formulations is the fact that chemicals having agricultural activity often exhibit extreme insolubility in water. This results in their having to be dissolved either in organic solvents or utilized in the form of emulsions or suspensions. With respect to the use of organic solvents, these are generally disadvantageous from an environmental and cost viewpoint. Particularly, such organic chemicals may exhibit toxicity or side-effects which may be adverse to the effect of the agricultural chemical itself or to the subsequent fruit or vegetable produced in the particular agricultural use. This toxicity may also be disadvantageous with respect to handling.

When attempts are made to provide emulsified or suspension formulations, difficulties are encountered with respect to providing a desirably high concentration of the agriculturally active ingredient. Thus, when such agriculturally active chemicals are formulated into an emulsion, it is difficult to maintain the emulsified state. This makes it difficult to maintain a uniform formulation, particularly, when the formulation is diluted with water for application to the plants.

Typically, for example, the agriculturally active ingredient is mixed with one or more of a variety of conventional solvents and an emulsifying agent to form a concentrate. This concentrate may be an emulsion, suspension, or solution. The concentrate is then stored until it is transported to the site of use or may simply be transported and stored at the site of use. In any event, the concentrate normally will undergo some period of storage until it is ready for use. Understandably, it is most desirable to be able to transport the agriculturally active ingredient at the highest concentration possible so as to minimize the volume of material which need be transported. By the same token, however, at the use site, it is normally not feasible to admix ingredients together or to process them other than to dilute the concentrate with water. Accordingly, it is important that the concentrate emulsify easily, i.e., exhibit good "bloom", upon the addition of water. In addition, at the use site, it is often necessary to store the diluted concentrate for extended time periods until the actual application to the plants. Consequently, it is important that the diluted form of the concentrate exhibit good stability with respect to the uniformity of the emulsion and to avoid precipitation of the active ingredients. If non-uniformity or precipitation occurs in the diluted form, then non-uniformity will result in the application of the diluted formulation to the plants.

Substantial progress in providing emulsifiable concentrates which avoid the problems of the prior art are disclosed in U.S. patent applications Ser. No. 448,707, filed Dec. 11, 1989, Ser. No. 505,030, filed Apr. 5, 1990, and Ser. No. 546,014, filed Jun. 28, 1990, the contents of all of which are incorporated herein by reference. The emulsifiable concentrates of these disclosures all require the presence of a hydrophobic solvent having the following Hansens' solubility parameters:

Dispersive component from about 56 to 75%;
Polar component from about 8 to 24%; and
H-bonding component of from about 10 to 30%.

This second component should also have surfactant properties and act as a non-ionic surfactant with an HLB value ranging from about 2 to 8. Examples of this solvent or component include alkylpyrrolidones having an alkyl portion containing from 6 to 14 carbon atoms, e.g., octylpyrrolidone, dodecylpyrrolidone, or N-(2'-ethylhexylpyrrolidone), alkyl gamma-butyrolactones, alkyl cyclic carbonates and combinations thereof, wherein the alkyl chains contain from 6 to 14 carbon atoms. The alkyl portion may be distributed at one or more sites on the ring so long as one portion contains at least 6 carbon atoms and the total number of alkyl carbon atoms does not exceed 14. For each of the above examples, the 6 to 14 carbon alkyl portions may be straight, branched, or cyclic, with straight chains being preferred. The preferred component or hydrophobic solvent is indicated as being long chain alkyl, and particularly those selected from pyrrolidones having the formula wherein $R_2$ is hydrogen or alkyl having from 6 to 14 carbon atoms and $R_3$ is alkyl having from 6 to 14 carbon atoms with the proviso that at least one of $R_2$ or $R_3$ must contain at least 6 carbon atoms and the sum of the carbon atoms in $R_2$ and $R_3$ cannot exceed 14.

SUMMARY OF THE INVENTION

We have discovered a novel emulsifiable concentrate of an agriculturally active chemical, which concentrate provides, upon dilution, a highly stable emulsion and avoids precipitation of the active ingredient on extended storage. In addition, the inventive emulsifiable concentrates may contain relatively high concentrations of the agriculturally active chemical, the concentration sometimes referred herein to as "loading", making it advantageous from both economic and handling viewpoints.

More particularly, the emulsifiable concentrate of the present invention is composed of an agriculturally active chemical, a surfactant, and a solvent selected from the group consisting of a first component having a sufficiently high hydrophilic property to solubilize the agriculturally active chemical, a second component which is a hydrophobic solvent, and a mixture thereof with the proviso that between about 5 to 90 weight percent of a compound having the structure:

wherein R' is alkyl having from five to eighteen carbon atoms, is present as the second component.

DETAILED DESCRIPTION OF THE INVENTION

Typical examples of first components suitable for use in the solvent are alkylpyrrolidones having from 1 to 4 carbon atoms in the alkyl group, cyclic lactones, e.g., gammabutyrolactones, lower alkyl cyclic carbonates, i.e., ethylene carbonate, propylene carbonate, butylene carbonate, lower alkylimidazolone, e.g., N-N,dimethylimidazolone, lower alkylamides of formic acid and acetic acid, e.g., dimethyl formamide and dimethylacetamide, and lower alkyl sulfoxides, e.g., dimethylsulfoxide. (The term "lower alkyl" in these examples means one or two carbons.) Mixtures of these may also be used as the first component.

Preferably, the first component is selected from the group consisting of pyrrolidones having the formula wherein R is hydrogen or lower alkyl having from 1 to 4 carbon atoms and R1 is lower alkyl having from 1 to 4 carbon atoms.

Examples of appropriate hydrophobic solvents include alkylpyrrolidones having an alkyl portion containing from 6 to 14 carbon atoms, e.g., octylpyrrolidone, dodecylpyrrolidone, or N-(2'-ethylhexylpyrrolidone), alkyl gammabutyrolactones, alkyl cyclic carbonates and combinations thereof, wherein the alkyl chains contain from 6 to 14 carbon atoms. The alkyl portion may be distributed at one or more sites on the ring so long as one portion contains at least 6 carbon atoms and the total number of alkyl carbon atoms does not exceed 14. Preferred 6 to 14 carbon alkyl portions are composed of straight chains. Branched or cyclic alkyl portions may also be used.

The hydrophobic solvent is preferably selected from pyrrolidones having the formula wherein R2 is hydrogen or alkyl having from 6 to 14 carbon atoms and R3 is alkyl having from 6 to 14 carbon atoms with the proviso that at least one of R2 or R3 must contain at least 6 carbon atoms and the sum of the carbon atoms in R2 and R3 cannot exceed 14.

However, in accordance with the invention, at least about 5 to 90 weight percent of the second component must be present in the form of an N,N-dimethyl amide of a carboxylic acid having at least six carbon atoms in the carboxyl component. Preferably, the amount of the amide is from about 15 to 45 weight percent, and most preferable from about 25 to 35 weight percent. Preferably, the alkyl group R1 as shown in structural formula I hereof has 5,6,9,11 or 17 carbon atoms therein. Also, mixture of these amides may be used. Typical of the amides which may be used are:

N,N-Dimethyl Caproamide (N,N-Dimethyl hexamide);
N,N-Dimethyl Caprylamide (N,N-Dimethyl octanamide);
N,N-Dimethyl Capramide (N,N-Dimethyl decanamide);
N,N-Dimethyl lauramide (N,N-Dimethyl dodecanamide); and
N,N-Dimethyl Myristamide (N,N-tetradecanamide).

These compounds are sold under the trademarks Halcomide by CP Hall. See CP Hall Company, technical bulletin no. 827733 (July, 1974). See also U.S. Pat. No. 3,342,673.

The inventive composition should contain one or more additional emulsifier(s) or surfactant(s) which is generally selected on a case by case basis in order to optimize the solubility and stability of the emulsion. Typically, such emulsifiers include ethoxylated alkyl phenols, linear aliphatic polyesters, linear aromatic polyesters, polyethoxylated alcohols, linear aliphatic ethoxylates, polyethoxylated castor oil, polyethoxylated carboxylates, and polyethoxylated alkylamines. Anionic surfactants may be used as the emulsifier and include phosphate esters and their sales, alkyl sulfonamides, salts of sulfated nonylphenoxypoly (ethyleneoxy) ethanol, salts of alkylbenzene sulfonates, also of alkylnaphthalene sulfonate, and sulfonated aliphatic polyesters and their salts. Also suitable are complex phosphate esters of nonionic surfactants of the ethylene oxide type which are mixtures of diesters of phosphoric acid. (See, for example, McCutcheon's, *Emulsifiers and Detergents* (1989), published by McCutcheon's Division of M.C. Publishing Co., Glen Rock, N.J.)

The inventive composition may further comprise an organic diluent which is a synthetic or naturally occurring oil having a high hydrophobic character or having a fractional dispersive solubility parameter of greater than 70% and preferably greater than 85% and a molar volume of greater than 90 cm$^3$/mole. These properties are defined in the C.R.C. Handbook referred to hereinabove. Typical diluents include soybean oil, rapeseed oil, long chain alcohols, long chain ketones, long chain esters, and ethers. As used herein, "long chain" means with 6 or more carbon atoms. Also suitable as the organic diluent are aromatic petroleum oils including those which are commercially available distillates from crude oils having an average boiling point greater than 200° C. Typical of such materials are those sold under the trademarks Exxon 200 or Texaco 400. Of course, such aromatics should be approved for use as a carrier for agriculturally active chemicals.

The composition of the aromatic petroleum oil is generally:

Heavy aromatic solvent naphtha—about 60%;
Middle distillate solvent extractant—about 40%.

Normally, these oils contain predominantly the $C_9$–$C_{15}$ aromatic hydrocarbons and primarily the $C_{10}$–$C_{12}$ hydrocarbons having a flash point of about 203° F.

The agriculturally active chemical (sometimes referred to herein as AAC) concentration should be as high as possible so long as it does not precipitate out upon dilution of the concentrate with water for a reasonable period of time and achieves the desired effect. Precipitation (crystal formation) on standing not only depletes the solution of AAC, it can also lead to fouling of application equipment, i.e., sprayers, etc. With the present invention, it is possible to obtain concentrates with agriculturally active chemical concentrations in excess of about 5 weight percent which form a stable emulsion upon being diluted with water. Preferably, the amount of AAC is from 5 to 30% and most preferably, 10 to 20%. The first component may be present in amount from about 0 to 90 percent, and the second component including the dimethylamide may be present in amounts from 5 to 90%, preferably 10 to 70% and most preferably, 20 to 50 percent with at least about 5 weight percent constituting the dimethylamide. The diluent may be present in amounts of from about 0 to 90% and the surfactant may be present in amounts from about 1 to 30%, preferably 5 to 25%, and most preferably, from 10 to 20%. AS used herein, all percents are percents by weight based on the total weight of the concentrate, unless otherwise specified.

As used herein, the term "agriculturally active chemical" includes compounds and mixtures thereof which can be used as agricultural fertilizers, nutrients, plant growth accelerants, herbicides, plant growth controlling chemicals, and chemicals which are effective in killing plants, insects, microorganisms, fungi, bacteria and the like which are commonly referred to as insecticides, bactericides, fungicides, nematocides, fumigants, and the like, as well as any other chemicals having properties which are suitable for agricultural uses in terms of application to plants or animals or domestic uses for controlling insects and pests. Particularly, such chemicals would normally take the form of water-immiscible or oily liquids and/or solids which is substantially insoluble in water. By the term "substantially insoluble", it is meant that for all practical purposes, the solubility of the compound in water is insufficient to make the compound practicably usable in an agricultural end use without some modification either to increase its solubility or dispersability in water, so as to increase the compound's bioavailability or avoid the use of excessively large volumes of solvent.

Suitable agriculturally active chemicals which can be used with the present invention include insecticides, such as, cyclocompounds, carbamates, animal and plant derivatives, synthetic pyrethroids, diphenyl compounds, non-phosphates, organic phosphates, thiophosphates, and dithiophosphates. (See *Agricultural Chemicals*, Book I, *Insecticides*, 1989 Revision by W. T. Thomson, Thomson Publications.) Typical of the insecticides are:

| | |
|---|---|
| cyclocompounds: | 6,7,8,9,10,10-hexachloro-1,5,5a,6,9,9a-hexahydro-6,9-methano-2,4,3-benzodioxathiepin-3-oxide |
| carbamates: | 2-isopropyl phenyl-N-methyl carbamate; 2-(1,3-dioxolan-2yl) phenylmethyl carbamate; 2,3-isopropylidine dioxyphenyl methyl carbamate; |
| animal and plant derivatives: | chlorinated hydrocarbons derived from Southern pine; naturally occurring lactone glycoside; |
| synthetic pyrethroids: | (±) α-cyano-3-phenoxybenzyl (±) cis, trans 3-(2,2-dichlorovinyl)-2,2-dimethyl cyclopropane carboxylate; (±) cyano (3-phenoxyphenyl methyl (±)-4-(difluoromethyoxy) α-(1-methylethyl) benzene acetate; |
| phenoxy compounds and non-phosphate: | 2,2-bis(p-methoxy phenyl)-1,1,1,trichloroethane; 1,3,5,tri-n-propyl-1,3,5-triazine-2,4,6 (1H,3H,5H) trione; ethyl (2E, 4E)-3,7,11-trimethyl-2,4-dodeca dienoate; 1-decycloxy 4-[(7-oxa-oct-4-ynyl)]-oxybenzene; |
| organic phosphates: | dimethyl phosphate ester of 3-hydroxy-N,N-dimethyl-cis-crotonamide; 2-chloro-1-(2,4-dichloro phenyl) vinyl diethylphosphate; 4-(methyl thio) phenyl dipropyl phosphate; |
| thiophosphates: | O,O-diethyl-O-4-nitrophenyl phosphorothioate; O,O-diethyl-O-(2,isopropyl-6-methyl-5-pyrimidinyl) phosphorothioate; 2-diethylamino-6-methyl pyrimidine-4-yl dimethyl phosphorothioate: |
| dithiophosphates: | O,O-dimethyl phosphorodithioate ester of diethylmercapto succinate; O-ethyl-S-phenyl ethyl phosphorodithioate. |

Typical herbicides include phenoxy compounds, benzoic, acetic, and phthalic acids, aniline derivatives, nitriles, amides, acetamides, anilides, carbamates, thiocarbamates, and heterocyclic nitrogen derivatives, e.g., triazines, pyridines, pyridazones, picolinic acid, and urea derivatives and phosphates. (See *Agricultural Chemicals*, Book II, *Herbicides*, 1986–87 Edition, W. T. Thomson, Thomson Publications, Fresno, Calif. 93791.) Exemplary of the above compounds are:

| | |
|---|---|
| phenoxy compounds: | 2,4-Dichlorophenoxy acetic acid 2,4,5-trichloro phenoxyacetic acid; 4-(2,4-dichlorophenoxy) butyric acid; S-ethyl 2 methyl-4-chlorophenoxy-thioacetate; 2-methyl-4-chloro-phenoxy acetic acid; methyl 5-(2,4-dichloro-phenoxy)-2-nitrobenzoate; |
| benzoic and acetic acids of phthalic compounds: | 3,6-dichloro-o-anisic acid 4-chloro-2-oxo benzothiazolin-3-yl acetic acid; |

| | -continued |
|---|---|
| nitriles and aniline derivatives: | N-1-Naphthyl-phthalamic acid; 3-5-dibromo-4-hydroxybenzonitrile; α,α,α,trifluoro-2,6-dinitro-N, N-dipropyl-p-tolidine; N-(1-ethylpropyl)-2,6-dinitro-3,4-xylidine; |
| amides, acetamides, anilides: | N,N-diethyl-2-(1-naphthalenyl oxy)-propionamide; 2,6-dimethyl-N-2' methoxy-ethyl-chloro-acetanilide; 3',4'-dichloro-propionanilide; α-chloracetic-N-(3,5,5-trimethyl-cyclohexen-1-yl)-N-isopropylamide; 4-benzyl-N-isopropyl trimethyl acetamide; |
| thiocarbamates: | S-Ethyl dipropyl thiocarbamate; |
| urea derivatives: | 3-(5-tert-butyl-3-isoxazoyl)-1,1-dimethyl urea; N-(2,6-trifluoro-benzoyl)-N,-[2,5-dichloro-4-(1,1,2,3,3,3-hexafluoropropyloxy) phenyl] urea; |
| pyrrolidone derivatives: | 1-(m-trifluoro methyl phenyl)-3-chloro-4-chloromethyl-2-pyrrolidone; |
| amino acid derivatives: | methyl N-benzoyl-N-(3-chloro-4-fluorophenyl)-DL alarinate; N-chloroacetyl-N-(2,6-diethyl phenyl)-glycine ethyl ester; |
| carbamates: | Isopropyl-m-chlorocarbanilate; 3-Ethoxy (carbonyl aminophenyl)-N-phenyl carbamate; |
| heterocyclics: | 4-amino-3,5-dichloro-6-fluoro-2-pyridyloxy acetic acid; 4-(1,2-Dimethyl-N-propyl amino)-2-ethyl amino-6-methyl thio-S-triazine; 2-[4,5-dihydro 4-methyl-4-(1-methyl ethyl)-5-oxo-1 H-imidazoyl-2yl-3-byridinecarboxylic acid; 2-[3,5-dichlorophenyl)-2-(2,2,2-trichloroethyl) oxinane; Butyl-9-hydro-fluorene-(9)-carboxylate; 2-[1-(ethoxy imino) butyl]-3-hydroxy-5-(2H-tetra hydro thio-pyran-3-yl)-2-cyclohexene-ione; 2-(2 chlorophenyl) methyl-4,4-dimethyl-3-iso oxazolidinone; |
| phosphates: | O-ethyl-O-(3-methyl-6-nitro phenyl) N-sec-butyl phosphoro thio amidate. |

Typical fungicides include (See *Agricultural Chemicals*, Book IV, *Fungicides*, 1989 Revision, W. T. Thomson, Thomson Publications, Fresno, Calif. 93791):

| | |
|---|---|
| organic compounds: | 2,5-dimethyl-N-Cyclohexyl-N-methoxy-3-furan carboxamide; 5-Ethyoxy-3-trichloromethyl-1,2,4-thiadiazole; 3-(2-methyl piperidino) propyl 3,4-dichlorobenzoate; N,N'-(1,4-piperazinediyl bis (2,2,2-trichloro) ethylidene) bis formamide; Tetramethyl thiuram disulfide; O-Ethyl-S,S,diphenyl-dithiophosphate; 5,10-dihydro-5,10-dioxo naphtho (2,3,9)-p-dithiin-2,3-dicarbonitrile; 2-(Thiocyano methyl thio) benzothiazole; α-2-(4-chlorophenyl) ethyl]-α-(1,1-dimethyl ethyl)-1 H-1,2,4-triazole-1-ethanol; |
| morpholines: | N-tridecyl-2,6-dimethyl morpholine; 4-N-dodecyl-2,6-dimethyl morpholine; |

Typical fumigants, growth regulators, repellents, and rodenticides include (See *Agricultural Chemicals*, Book III, *Fumigants*, 1988-1989 Revision, W. T. Thomson, Thomson Publications, Fresno, Calif. 93791):

| | |
|---|---|
| growth regulants: | 1,2 Dihydro-6-ethyoxy-2,2,4-trimethylquinoline; (2-chloroethyl) phosphoric acid; 4-[acetamino) methyl]-2-chloro-N (2,6-diethyl phenyl) acetamide; Benzoic acid, 3,6 dichloro-2-methoxy,2-ethoxy-1-methyl-2-oxo ethyl ester: |
| repellents: | O,O-dimethyl-O-[(4-methyl thio)-m-tolyl] phosphorothioate; Tetriary butyl-sulfenyl dimethyl dithio carbamate; |
| seed softener: | 2-chloro-6-(trichlomethyl) pyridine; 5-ethoxy-3-trichloromethyl-1,2,4-thiadiazole; N-phenyl-N'-1,2,3-thiadiazol-5-yl urea; |

Pesticides may be characterized by their physical properties, depending on their physical state at normal or ambient conditions, i.e., between 40° F. and 90° F. and their solubility or miscibility with water or other common organic solvents, e.g., aromatics, such as, toluene, xylene, methylated and polyalkylated naphthalenes, and aliphatic solvents.

Based on the physical properties, the pesticides may be classified into two groups. The first group includes those which are oily liquids at ambient temperatures and are immiscible with water. Specific pesticides include:

Common esters of 2,4-dichlorophenoxyacetic acid,
Common esters of 2,4,5-trichlorophenoxyacetic acid,
Common esters of 2-(2,4-dichlorophenoxy) propionic acid,
Common esters of 2-(2,4,5-trichlorophenozy) propionic acid,
Common esters of 2,4-dichlorobutyric acid,
Common esters of 2,methoxy-3,6-dichlorobenzoic acid,
Common esters of 2-methyl-4-chlorophenoxyacetic acid,
Piperonyl butoxide 3,4-methylenedioxy-6-propyl benzyl n-butyl diethylene glycol ether,
Bromophos ethyl: 0,0-diethyl-0-2,5-dichloro-4-bromophenyl thionophosphate,
N-(2-mercaptoethyl) benzene-sulfenamide (BETASAN®),
Isobornyl Thiocyanoacetate (THANITE),
Ioxynil ester of octanoic acid,
Molinate S-ethyl hexahydro - 1 H - azepine-1-carbothioate,
PP 511 0,0-dimethyl-(2-diethylamine 4-methyl-6-pyrimidinyl) carbamate,
PP 211 0,0-diethyl O-(2-diethylamine-4-methyl-6-pyrimidinyl) phosphorocarbamate,
Chlordane
5-Ethoxy-3-(trichlorometyl)-1,2,4-thiadiazole (TERRAZALE®), Ethyl-s-s-dipropyl-phosphodithioate (MOCAP®),
S-Ethyl dipropylthiocarbamate (EPTAM®),
S-Ethyl diisobutylthiocarbamate (SUTAN®),
S-n. propyl-di-n-propylthiocarbamate (VERNAM®),
S-propyl butylethylthiocarbamatae (TILLAM®),
S-ethyl ethylcyclohexylthiocarbamate (RO-NEET®),
Malathion (S-(1,2-dicarboxyethyl)-0,0-dimethyl phosphorodithioate),
Diazinon (0,0-diethyl,0-(2-isopropyl-4-methyl-6-pyrimidinyl) phosphorothioate,
O-Ethyl-S-phenyl-ethylphosphonodithioate (DYFONATE®),
Toxaphene (Octachlorocamphene),
Bromoxynil (3,5-dibromo-4-hydroxy benzonitrile ester of n.octanoic acid,
2-chloro-N-2,6-diethylphenyl-N-methoxymethylacetamide (LASSO®),
Diallate S-2,3-dichloroallyl N,N-diisopropylthiolcarbamate,
aTriallate S-2,33-trichloroallyl N,N-diisopropylthiolcarbamate.

The second group comprises those pesticides which are solids at ambient temperatures and for all practical purposes, insoluble in water.

2,4,5-T (2,4,5-trichlorophenoxy acetic acid)
Monuron (3-(p-chlorophenyl)-1,1-dimethyl urea)
Diuron (3-(3,4-dichlorophenyl)-1,1-dimethyl urea)
Bromacil (5 bromo-3-sec. butyl-6-methyl uracil)
Isocil (5 bromo-3-isopropyl-6-methyl uracil)
Linuron (3-(3,4 dichlorophenyl)-1-methoxy-1 methyl urea
Atrazine (2-chloro-4-ethylamino-6 isopropylamino-s-trriazine) Simazine (2-chloro-4,6,-bis (ethylamino)-s-triazine
Dodine (n-dodecylguanidine acetate)
Thiram (tetramethylthiuram disulfide)
N-(mercaptomethyl)phthalimide s-(o,o dimethylphosphorodithioate) (IMIDAN®)
Lindane (gamma 1,2,3,4,5,6 hexachlorocyclohexane)
Folpet (N-trichloromethylphthalimide)
Manazon (s-(4,6-diamino-1,3,5-triazin-2-yl methyl)-dimethyl phosphorothiolthionate)
Barban (4-chloro-2 butynyl m-chlorocarbanilate)
Tricumba 2-methoxy-3,5,6-trichlorobenzoic acid
Trifluralin (2,6-dinitro-N,N-dipropyl-4-trifluoromethylaniline) (2,3 dihydro-5-carboxanilido-6-methyl-1,4-oxathiin) (VITAVAX®)
0 2,4-dichlorophenoxyacetic acid
4-(4-chloro-2 methylphenoxy) butyric acid
2-(2,4-dichlorophenoxy) propionic acid
Ioxynil: 3,5 diiodo-4-hydroxybenzonitrile
Bromoxynil: 3,5 dibromo-4-hydroxybenzonitrile
Carbaryl: 1-naphthyl-N-methylcarbamate
Methoxychlor: 2,2,-Bis(p-methoxyphenyl)-1,1-trichloroethane
PP 781: 4(2-chloro phenylhydrazono)-3-methyl-5-isoxazolone*
PP 675: 5-butyl-2-dimethylamino-4-hydroxy-6-methyl pyrimidine*
PP 062: 5,6-dimethyl-2-dimethylamino-4 pyrimidinyl dimethylcarbamate*
PP 149: 5-n-butyl-2 ethylamino-4-hydroxy-6 methyl pyrimidine*

* Manufactured by Imperial Chemical Industries Limited

C 6313 N'-(4-bromo-3-chlorophenyl)-N-methoxy-N-methylurea
C 6989 2,4'dinitro-4-trifluoromethyl-diphenylether
Chloroxuron N'-4-(chlorophenoxy) phenyl-NN-dimethylurea
Dichlobenil 2,6-dichlorobenzonitrile
Diphenamid NN-dimethyl-2,2-diphenylacetamide
Fenac 2,3,6-trichlorophenylacetic acid
Fluometuron N,-(3-trifluoromethylphenyl)-NN-dimethylurea
GS 14260 4-ethylamino-2-methylthio-6-t-butyl-amino-1,3,5-triazine
PCP Pentachlorophenol
Lenacil 3-cyclohexyl-6,7-dihydro-1H-cyclo-pentapyrimidine-2,4-(3H,5H)-dione
Pyrazon 5-amino-4-chloro-2-phenyl-3-pyridazone
Metrobromuron N'-(4-bromophenyl)-N-methoxy-N-methylurea
Metoxymarc N-(4-methoxybenzoyl)-N-(3,4-dichlorophenyl)-N',N'-dimethylurea
Neburon N-butyl-N'-(3,4-dichlorophenyl-N-methylurea
NIA 11092 1,1-dimethyl-3-[3-(n-t-butyl carbamyloxy)-phenyl]urea
Mecoprop 2-(4-chloro-2 methylphenoxy)propionic acid
Monolinuron N,-(4-chlorophenyl)-N-methoxy-N-methylurea
Nitrofen 2,4-dichlorphenyl 4-nitrophenylether
Propanil N-(3,4-dichlororphenyl)propionamide
Pyriclor 2,3,5-trichloro-4-pyridinol
Solan 3'-chloro-2-methyl-p-volerotoluidide
Terbacil 5-chloro-3-t-butyl-6-methyluracil
UC 22463 (SIRMATE)-3,4-dichlorobenzyl N-methylcarbamate
WL 9385 2-Azido-4-ethylamino-6-t-butylamino-s-triazine
Propachlor 2-chloro-N-isopropylacetanilide
CP 50144 2-chloro-N-2,6-diethylphenyl-N-methoxymethylacetamide
CP 31675 2-chloro-N-(2 methyl-6-t-butylphenyl)acetamide
Cypromid 3',4'-dichlorocyclopropane carboxanilide
Fenuron NN-dimethyl-N,phenylurea
Chlorbromuron N'-(4-bromo-3-chlorophenyl)-N-methoxy-N-methylurea
Ametryne 2-methylmercapto-4-ethylamino-6-isopropyl-amino-s-triazine
Prometryne 2-methylmercapto-4,6-bisisopropyl amino-s-triazine
DCPA dimethyl 2,3,5,6, tetrachloroterephthalate
Benefin N-butyl-N-ethyl-a,a,atrifluoro-2,6-dinitro-p-toluidine
Nitralin 2,6-dinitro-4-methylsulfonyl-N,N-dipropyl-aniline
PP 493 2,6-difluoro-3,5-dichloro-4-hydroxy pyridine
CNP 2,4,6-trichlorophenyl-4,-nitrophenyl ether
Pentachloro nitrobenzine
1-(butile carbamoyl)-2-benzimidazol carbamic acid, methyl ester (BENLATE®).

EXPERIMENTAL PROCEDURE

Formulations

Formulations were prepared by weighing the exact proportion of ingredients and mixing them together in a bottle. The solvents were weighed first. The AAC was dissolved completely in the solvent system followed by addition of the surfactant or emulsifying agent. Typically, about 10g of each of the formulations was prepared.

The contents were stirred well in an automatic rocking shaker for about 30 minutes and until the AAC dissolved completely. The samples thus prepared were evaluated for freeze-thaw stability on storage and ease of emulsification and emulsion stability on dilution. For dilution, 2 grams of concentrate were diluted to 50 grams using World Health Organization (WHO) standard (6 g of $CaCl_2$ and 2.78g of $MgCl_2 6H_2O$ dissolved in 20 L) hard water having a hardness of 342 ppm expressed as $CaCO_3$ equivalent.

Freeze-Thaw Stability

The concentrates were stored for a period of 24 hours in the cold (temperature 5° C.) in a refrigerator and taken out and thawed to room temperature and then stored at 55° C. in an oven for a period of 24 hours. The alternate storage in the cold (5° C.) and warm condition at 55° C. was repeated for three cycles. Any separation during the storage was recorded. A concentrate is "stable" if there is no substantial separation after the 24 hour cycles at each temperature. All of the solutions exemplified hereinafter exhibited stability according to this test between the temperatures of 5° C. and 55° C. Some of the solutions were even stable at a lower range of −5° C.

Evaluation of Emulsion Stability and Ease of Emulsification

A Nessler tube 1.8 cm diameter; 28 cm long) was filled with an appropriate quantity (47–48 g) of WHO water. (World Health Organization (WHO) standard (6 g of $CaCl_2$ and 2.78 g of $MgCl_2 6H_2O$ dissolved in 20 L) hard water having a hardness of 342 ppm expressed as Na equivalent.) Using a serological pipette, 0.5–2.5 g of emulsion concentrate was dropped into the Nessler tube containing 47.5–49.5 g water. The initial bloom was observed at zero time without stirring and the quality of the bloom was graded by visual appearance as shown below. The Nessler tube was stopped and inverted 20 times; the bloom was again recorded and so also stability as judged by volume or height of the sedimentation (cream/ppt/oil) followed at different intervals of time: 0, 1 hour, 2 hours, up to 24 hours.

Determination of A.A.C. Solubility

A weighed quantity of the A.A.C. was stirred with 10 grams of the chosen solvent in an automatic rocking shaker for 30 minutes. From 0.1 to 1 g. of the A.A.C. was used depending on its solubility. Incremental 0.1 g amounts of the AAC added until no further dissolution based on the clarity of the solutions was obtained. Increments of the solvent in 0.1 g. amounts were added until the solution was clear to determine the lower end of solubility. All determinations were made at ambient temp (20–25 C.).

Stability of Diluted Concentrate:

The composition of the concentrate (EC) diluted with water was considered "stable" if at EC concentrations of from 0.2 to 1%, the composition after mixing (twenty inversions) exhibited two mm or less cream and no oil in one hour. Both the top and bottom of the tube were checked.

| Bloom: | |
|---|---|
| Excellent | Thick emulsion cloud with no separation |
| Good | Emulsion cloud may be thin, or may ex- |

| Bloom: | |
|---|---|
| | hibit trailing, small number of oil droplets within cloud |
| Poor | Many oil droplets within cloud, some droplets separate from cloud |

Each of the emulsifiable concentrates thus prepared were analyzed for ease of emulsification (bloom) upon addition of water and after twenty inversion of the sample as well as emulsion stability upon dilution with water. The composition of the samples and the results of the analysis are set forth in the following tables.

Crystal Formation Studies

A number of the samples were evaluated for precipitation of AAC, i.e., crystal growth over varying time periods. This was done using the following techniques:

1. The diluted sample was placed in a 100 ml beaker and stirred continuously. Aliquots were removed at 1, 4, 7, and/or 24 hour intervals and examined under 250× magnification, using a 2×2 mm slide, which provided 1500 separate viewing areas. The number of crystals, if any, in ten different viewing areas were counted and averaged. If no crystals were found, second and third aliquots were examined.

2. The remaining portion of the diluted sample was passed through U.S. Standard screens (60, 100 and 250 mesh) and sediment retained is reported.

3. The diluted sample was allowed to stand without stirring for 24 hours and inverted twenty times. An aliquot of the inverted sample was examined under 250× and the results reported as above. The remaining portion was passed through screens and retained sediment reported.

The components set forth in the Tables are referred to by their commercial names for purposes of brevity. The chemical nomenclature of the materials is as follows:

| | |
|---|---|
| LP-100 | N-octylpyrrolidone |
| LP-300 | N-dodecylpyrrolidone ($C_{12}$ chain) |
| LP-940 | N-octadecylpyrrolidone ($C_{18}$ chain) |
| Gafac RM 710 | Poly(oxy-1,2-ethanediyl)α-(dinonylphenyl)-omega-hydroxy-phosphate. |
| Igepal CO-630 | Ethoxylated nonyl phenol containing 9 EO units |
| Thidiazuron | 1-phenyl-3-(1,2,3-thiadiazol-5-yl)urea |
| Gafac RE-610 | Poly(oxy-1,2-ethanediyl)α-(nonylphenyl)-ω-hydroxy-poly(oxy-1,2-ethanediyl) phosphate |
| Silwet L-77 | (Silwet copolymer L-77) nonionic organo silicone (Union Carbide) |
| Silwet L-7607 | (Silwet copolymer L-7607) nonionic organo silicone (Union Carbide) |
| Pegol L-31 | Ethoxylated polyoxy propylene |
| Atrazine | 6-chloro-N-ethyl-N'-(1-methyl ethyl)-1,3,5, triazine-2,4-diamine |
| Carbaryl | 1-Naphthalenyl methyl carbamate |
| Pendimethalin | N-(1-ethylpropyl)-3,4-dimethyl-2,6-dinitrobenzenamine |
| Prodiamine | 2,4-dinitro-$N^3,N^3$-dipropyl-6-(trifluoromethyl)-1,3-benzene diamine |
| Thidiazuron | N-phenyl-N'-1,2,3-thiadiazol-5-ylurea |
| Thidiazuron | 1-phenyl-3-(1,2,3-thiadiazol-5-yl)urea |
| Triforine | N,N'-[1,4-piperazine diyl bis (2,2,2-trichloro ethylidene)] bisformamide |
| CGA184699 | N-(2,6-trifluorobenzoyl)-N'-[2,5-dichloro-4-(1,1,2,3,3,3hexafluro-propyloxy)-phenyl]urea |
| Fungicide SXX 0665 | Triazine derivative, experimental fungicide (Bayer) |
| Exxon 100 | Light aromatic solvent naphtha |

| | -continued |
|---|---|
| Exxon 150 | (petroleum) consists predominantly of $C_8$-$C_{10}$ aromatic hydrocarbons; boiling point range 152–168° C. Heavy aromatic solvent naphtha (petroleum) consists predominantly of $C_9$-$C_{11}$ aromatic hydrocarbons; boiling point range 176–210° C. |
| Exxon 200 | Heavy aromatic solvent naphtha (petroleum) consists predominantly of $C_9$-$C_{15}$ aromatic hydrocarbons; boiling point range 217–293° C. |
| Halcomide M-8-10 | 5% N,N-Dimethyl hexamide 50% N,N-Dimethyl octanamide 40% N,N-Dimethyl decanamide 5% N,N-Dimethyl lauramide |
| Halcomide M-12 | 2% N,N-Dimethyl decamide 95% N,N-Dimethyl dodecanamide 3% N,N-Dimethyl tetradecanamide |

In the tables, SUPER refers to the upper layer on separation and PCPT refers to the bottom layer.

EXAMPLE 1

The relative solubilities of a number of AAC's were determined in a variety of solvents. The results are shown in Table I.

TABLE I

Relative Solubilities of AAC's in Various Solvents

| AAC | NMP | LP-100 | Halcomide M8-10 | LP-300 |
|---|---|---|---|---|
| Atrazine | 20–24 | 12–16 | 6–9 | 9–10 |

TABLE I-continued

Relative Solubilities of AAC's in Various Solvents

| AAC | NMP | LP-100 | Halcomide M8-10 | LP-300 |
|---|---|---|---|---|
| Prodiamine | 33–42 | 28–32 | 18–22 | 19–21 |
| Triforine | 34–36 | 13–18 | 6–8 | 7–10 |
| Thidiazuron | 13–15 | 21–23 | 5–6 | 13–16 |
| Carbaryl | 45–48 | 24–32 | 20–24 | 16–20 |
| CGA 184699 | >61 | 48–49 | >34 | 40–41 |
| Fungicide SXX 0665 | 48 | 22–27 | >19 | 13–19 |
| Pendimethalin | 66–68 | 42–45 | 48–49 | >44 |

EXAMPLE 2

A series of emulsion concentrates were prepared using a variety of solvents and dimethyl amides. The quality and stability of the emulsions obtained on dilution and stirring were evaluated. The results are shown in table II. Table III shows the results of crystal growth evaluations produced from the emulsified concentrates after dilution and stirring for 24 hours.

In the tables, the symbols have the following meanings: * S=Soluble; IS=Insoluble; PS Hazy; Mostly Soluble, 2.5 g Concentrates were diluted with WHO Standard 342 ppm Hard Water to 50 g.; - Means No Sediment; +Means Trace; ++Means <1%; +++Means 1–5%; * 0 Means no crystals; # Means 0–10 crystals per view; ##10–100 crystals per view; ###100–1000 crystals per view. 1 slide 2×2cm=2500 views. Exc. means Excellent

TABLE II

| | COMPONENT | | | | | |
|---|---|---|---|---|---|---|
| | 1 | 2 | 3 | 4 | 5 | 6 |
| COMPOSITION | | | | | | |
| N-Methylpyrrolidone (M-Pyrol) | 36.0 | 9.75 | 29.3 | 24.8 | 0.0 | 0.0 |
| Halcomide M-8-10 | 27.0 | 40.50 | 13.3 | 11.3 | 75.0 | 37.5 |
| N-Octyl Pyrrolidone (Lp-100) | 0.0 | 0.0 | 0.0 | 0.0 | 0.0 | 0.0 |
| N-Dodecyl Pyrrolidone (Lp-300) | 0.0 | 0.0 | 0.0 | 0.0 | 0.0 | 37.5 |
| Aromatic Oil (Exxon 200) | 27.0 | 24.75 | 10.6 | 9.0 | 0.0 | 0.0 |
| Gafac RE 610 | 5.0 | 10.0 | 16.8 | 20.0 | 10.0 | 10.0 |
| (A.A.C.) Atrazine | 5.0 | 0.0 | 0.0 | 0.0 | 0.0 | 0.0 |
| Prodiamine | 0.0 | 15.0 | 0.0 | 0.0 | 0.0 | 0.0 |
| Pendimethalin | 0.0 | 0.0 | 30.0 | 34.9 | 0.0 | 0.0 |
| Triazine Derivative | 0.0 | 0.0 | 0.0 | 0.0 | 15.0 | 15.0 |
| TOTAL | 100.0 | 100.0 | 100.0 | 100.0 | 100.0 | 100.0 |
| *Solubility @ 23 C. | S | S | S | S | S | S |
| RESULTS | | | | | | |
| EMULSION BLOOM:* | | | | | | |
| 0-TIME | Exc.* | Exc. | Exc. | Exc. | None Exc. | None Exc. |
| AFTER 20 TURNS | Exc. | Exc. | Exc. | Exc. | | |
| SOLIDS CREAMS OR OIL mm: | SUPER / PCPT | SUPER / PCPT | SUPER / PCPT | SUPER / PCPT | SUPER / PCPT | SUPER / PCPT |
| 0-TIME 20 AFTER TURNS | 0 / 0 | 0 / 0 | 0 / 0 | 0 / 0 | 0 / 0 | 0 / 0 |
| ONE HOUR | 0 / 0 | 0 / 0 | 0 / trace | 0 / trace | 3 / 0 | 3 / 0 |
| TWO HOURS | 0 / 0 | 0 / 0 | 0 / 1 | 0 / trace | 6 / 0 | 6 / 0 |
| FOUR HOURS | 3 / 0 | 0 / 0 | 0 / 1 | 0 / trace | 11 / 0 | 7 / 0 |
| 24 Hours | 8 / 0 | 0 / trace | 0 / 1 | 0 / 1 | 14 / 0 | 20 / 0 |
| After 20 Turns Observed under microscope @ 250X mag after 24 hrs. | | | | | | |
| Filtered Through Screens | | | | | | |
| 60 Mesh | # | # | 0 | 0 | 0 | 0 |
| 100 Mesh | + | − | − | − | − | − |
| 250 Mesh | − | − | − | + | − | − |
| | − | − | − | + | − | − |

| | COMPONENT | | | | | |
|---|---|---|---|---|---|---|
| | 7 | 8 | 9 | 10 | 11 | 12 |
| COMPOSITION | | | | | | |
| N-Methylpyrrolidone (M-Pyrol) | 0.0 | 37.5 | 37.5 | 37.5 | 22.5 | 15.0 |
| Halcomide M-8-10 | 37.5 | 37.5 | 18.75 | 9.75 | 18.75 | 15.0 |
| N-Octyl Pyrrolidone (Lp-100) | 0.0 | 0.0 | 0.0 | 0.0 | 0.0 | 0.0 |
| N-Dodecyl Pyrrolidone (Lp-300) | 0.0 | 0.0 | 0.0 | 9.0 | 18.75 | 15.0 |
| Aromatic Oil (Exxon 200) | 37.5 | 0.0 | 18.75 | 18.75 | 15.0 | 30.0 |

TABLE II-continued

| | | | | | | |
|---|---|---|---|---|---|---|
| Gafac RE 610 | 10.0 | 10.0 | 10.0 | 10.0 | 10.0 | 10.0 |
| (A.A.C.) Atrazine | 0.0 | 0.0 | 0.0 | 0.0 | 0.0 | 0.0 |
| Prodiamine | 0.0 | 0.0 | 0.0 | 0.0 | 0.0 | 0.0 |
| Pendimethalin | 0.0 | 0.0 | 0.0 | 0.0 | 0.0 | 0.0 |
| Triazine Derivative | 15.0 | 15.0 | 15.0 | 15.0 | 15.0 | 15.0 |
| TOTAL | 100.0 | 100.0 | 100.0 | 100.0 | 100.0 | 100.0 |
| *Solubility @ 23 C. | S | S | S | S | S | S |

RESULTS

EMULSION BLOOM:*

| | | | | | | | | | | | | |
|---|---|---|---|---|---|---|---|---|---|---|---|---|
| 0-TIME | Exc. | | Poor | | Exc. | | Good | | Fair | | Good | |
| AFTER 20 TURNS | Exc. | | Exc. | | Exc. | | Exc. | | Exc. | | Exc. | |
| SOLIDS CREAMS OR OIL mm: | SUPER | PCPT | SUPER | PCPT | SUPER | PCPT | SUPER | PCPT | SUPER | PCPT | SUPER | PCPT |
| 0-TIME 20 AFTER TURNS | 0 | 0 | 0 | 0 | 0 | 0 | 0 | 0 | 0 | 0 | 0 | 0 |
| ONE HOUR | 0 | 0 | 0 | 0 | 0 | 0 | 0 | 1 | 0 | 0 | 0 | 0 |
| TWO HOURS | 0 | 0 | 0 | 0 | 0 | 1 | 0 | 2 | 0 | 0 | 0 | 1 |
| FOUR HOURS | 0 | 0 | 0 | 0 | 0 | 1 | 0 | 2 | 0 | trace | 0 | 2 |
| 24 Hours | 0 | 0 | 5 | 1 | 0 | 1 | 0 | 5 | 0 | 2 | 0 | 5 |

***After 20 Turns
Observed under microscope
@ 250X mag after 24 hrs.

| | | | | | | | | | | | | |
|---|---|---|---|---|---|---|---|---|---|---|---|---|
| Filtered Through Screens | 0 | | 0 | | ## | | ## | | 0 | | 0 | |
| 60 Mesh | — | | ++ | | +++ | | +++ | | — | | — | |
| 100 Mesh | — | | + | | ++ | | ++ | | — | | — | |
| 250 Mesh | — | | + | | ++ | | + | | — | | — | |

| | COMPONENT | | | | |
|---|---|---|---|---|---|
| | 13 | 14 | 15 | 16 | 17 |
| COMPOSITION | | | | | |
| N-Methylpyrrolidone (M-Pyrol) | 0.0 | 52.5 | 0.0 | 7.8 | 3.9 |
| Halcomide M-8-10 | 22.5 | 7.55 | 35.5 | 39.0 | 37.7 |
| N-Octyl Pyrrolidone (Lp-100) | 0.0 | 0.0 | 9.5 | 0.0 | 0.0 |
| N-Dodecyl Pyrrolidone (Lp-300) | 22.5 | 7.5 | 0.0 | 0.0 | 0.0 |
| Aromatic Oil (Exxon 200) | 30.0 | 7.5 | 30.0 | 18.2 | 23.4 |
| Gafac RE 610 | 10.0 | 10.0 | 10.0 | 15.0 | 15.0 |
| (A.A.C.) Atrazine | 0.0 | 0.0 | 0.0 | 0.0 | 0.0 |
| Prodiamine | 0.0 | 0.0 | 0.0 | 0.0 | 0.0 |
| Pendimethalin | 0.0 | 0.0 | 0.0 | 0.0 | 0.0 |
| Triazine Derivative | 15.0 | 15.0 | 15.0 | 20.0 | 20.0 |
| TOTAL | 100.0 | 100.0 | 100.0 | 100.0 | 100.0 |
| *Solubility @ 23 C. | S | S | S | S | S |

RESULTS

EMULSION BLOOM:*

| | | | | | | | | | | |
|---|---|---|---|---|---|---|---|---|---|---|
| 0-TIME | Fair | | Fair | | Good | | | | | | |
| AFTER 20 TURNS | Exc. | | Exc. | | Exc. | | | | | | |
| SOLIDS CREAMS OR OIL mm: | SUPER | PCPT | SUPER | PCPT | SUPER | PCPT | SUPER | PCPT | SUPER | PCPT | |
| 0-TIME 20 AFTER TURNS | 0 | 0 | 0 | 0 | 0 | 0 | 0 | 0 | NA | NA | |
| ONE HOUR | 0 | 0 | 0 | 0 | 0 | 0 | 0 | 0 | NA | NA | |
| TWO HOURS | 0 | 0 | 0 | 2 | 0 | 0 | 0 | 1 | NA | NA | |
| FOUR HOURS | 0 | 0 | 0 | 8 | 0 | 0 | 0 | 3 | NA | NA | |
| 24 Hours | 7 | 0 | 0 | 8 | 2 | 0 | 0 | 5 | NA | NA | |

***After 20 Turns
Observed under microscope
@ 250X mag after 24 hrs.

| | | | | | |
|---|---|---|---|---|---|
| Filtered Through Screens | 0 | ## | 0 | # | NA |
| 60 Mesh | — | +++ | — | + | NA |
| 100 Mesh | — | ++ | — | — | NA |
| 250 Mesh | — | +++ | — | — | NA |

*The descriptions have the following meanings:
excellent - complete emulsification obtained. Thick emulsion cloud with no separation.
good - emulsion cloud may be thin, or may exhibit trailing, small number of oil droplets within cloud.
poor - many oil droplets within cloud, some droplets separate from cloud.

TABLE III

Microscopic Observation for Crystal Growth from Selected Formulations

*Run No × 250

| | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| Time: | | | | | | | | | | | | | | | | | |
| 0 hrs | 0 | 0 | 0 | 0 | 0 | 0 | 0 | # | # | # | 0 | 0 | 0 | ## | 0 | 0 | NA |
| 1 hrs | 0 | 0 | 0 | # | 0 | 0 | 0 | ## | ## | ## | 0 | 0 | 0 | ## | 0 | 0 | NA |
| 4 hrs | # | 0 | 0 | ## | 0 | 0 | 0 | ## | ## | ## | 0 | 0 | 0 | ## | 0 | 0 | NA |
| 24 hrs | ## | ## | 0 | ## | 0 | 0 | 0 | ## | ## | ## | 0 | 0 | 0 | ## | 0 | ## | NA | after 24 hours Stirring
Filtered Through Screens:

| | | | | | | | | | | | | | | | | | |
|---|---|---|---|---|---|---|---|---|---|---|---|---|---|---|---|---|---|
| 60 Mesh | — | — | — | — | — | — | — | — | — | — | — | — | — | — | — | — | NA |
| 100 Mesh | — | — | — | — | — | — | — | — | — | + | — | — | — | — | — | — | NA |

TABLE III-continued

Microscopic Observation for Crystal Growth from Selected Formulations

*Run No × 250

| | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| 250 Mesh | + | − | − | − | − | − | − | + | + | + | − | − | − | + | − | + | NA |

EXAMPLE 3

A series of samples similar to those of Example 2 were prepared with the exception that no dimethyl amide was used. The results of these evaluations are shown in Tables IV and V.

TABLE IV

| | COMPONENT | | | | |
|---|---|---|---|---|---|
| | 18 | 19 | 20 | 21 | 22 |
| COMPOSITION | | | | | |
| N-Methylpyrrolidone (M-Pyrol) | 29.3 | 24.8 | 36.0 | 9.75 | 7.8 |
| Halcomide M-8-10 | 0.0 | 0.0 | 0.0 | 0.0 | 0.0 |
| N-Octyl Pyrrolidone (Lp-100) | 13.3 | 11.3 | 27.0 | 40.5 | 39.0 |
| N-Dodecyl Pyrrolidone (Lp-300) | 0.0 | 0.0 | 0.0 | 0.0 | 0.0 |
| Aromatic Oil (Exxon 200) | 10.6 | 9.0 | 27.0 | 24.75 | 18.0 |
| Gafac RE 610 | 16.8 | 20.0 | 5.0 | 10.0 | 15.0 |
| A.A.C. Atrazine | 0.0 | 0.0 | 5.0 | 0.0 | 0.0 |
| Prodiamine | 0.0 | 0.0 | 0.0 | 15.0 | 0.0 |
| Pendimethalin | 30.0 | 34.9 | 0.0 | 0.0 | 0.0 |
| Triazine Derivative | 0.0 | 0.0 | 0.0 | 0.0 | 20.0 |
| TOTAL | 100.0 | 100.0 | 100.0 | 100.0 | 100.0 |
| *Solubility @ 23 C. | S | S | S | S | S |
| | | RESULTS | | | |
| EMULSION BLOOM: | | | | | |
| 0-Time: | Exc. | Exc. | Exc. | Good | Hazy |
| After 20 Turns: | Exc. | Exc. | Exc. | Exc. | Exc. |
| SOLID CREAMS OR OIL (mm) | SUPER PCPT | SUPER PCPT | SUPER PCPT | SUPER PCPT | SUPER PCPT |
| 0-TIME 20 AFTER TURNS | 0   0 | 0   0 | 0   0 | 0   trace | 0   trace |
| ONE HOUR | 0   0 | 0   trace | 0   0 | 0   trace | 0   0 |
| TWO HOURS | 0   0 | 0   trace | trace   0 | 0   2 | 0   1 |
| FOUR HOURS | 0   0 | 0   trace | 1   0 | 0   4 | 0   3 |
| 24 hours | 0   0 | 0   trace | 6   0 | 0   5 | 0   5 |
| ***After 20 turns Observed under microscope @ 250X mag. after 24 hrs. Filtered Through Screens | 0 | 0 | 0 | 0 | 0 |
| 60 Mesh | − | trace | − | − | − |
| 100 Mesh | − | trace | − | − | − |
| 250 Mesh | − | − | − | − | − |

| | COMPONENT | | | |
|---|---|---|---|---|
| | 23 | 24 | 25 | 26 |
| COMPOSITION | | | | |
| N-Methylpyrrolidone (M-Pyrol) | 7.8 | 9.0 | 0.0 | 0.0 |
| Halcomide M-8-10 | 0.0 | 0.0 | 0.0 | 0.0 |
| N-Octyl Pyrrolidone (Lp-100) | 33.8 | 45.0 | 75.0 | 37.5 |
| N-Dodecyl Pyrrolidone (Lp-300) | 0.0 | 0.0 | 0.0 | 0.0 |
| Aromatic Oil (Exxon 200) | 23.4 | 21.0 | 0.0 | 37.5 |
| Gafac RE 610 | 15.0 | 10.0 | 10.0 | 10.0 |
| A.A.C. Atrazine | 0.0 | 0.0 | 0.0 | 0.0 |
| Prodiamine | 0.0 | 0.0 | 0.0 | 0.0 |
| Pendimethalin | 0.0 | 0.0 | 0.0 | 0.0 |
| Triazine Derivative | 20.0 | 20.0 | 15.0 | 15.0 |
| TOTAL | 100.0 | 100.0 | 100.0 | 100.0 |
| *Solubility @ 23 C. | S | S | S | S |
| | | RESULTS | | |
| EMULSION BLOOM: | | | | |
| 0-Time: | Hazy | | | |
| After 20 Turns: | Exc. | | | |
| SOLID CREAMS OR OIL (mm) | SUPER PCPT | SUPER PCPT | SUPER PCPT | SUPER PCPT |
| 0-TIME 20 AFTER TURNS | 0   trace | 0   1 | 0   0 | 0   0 |
| ONE HOUR | 0   2 | 0   2 | 0   0 | 0   0 |
| TWO HOURS | 0   2 | 0   3 | 2   0 | 0   1 (oil) |
| FOUR HOURS | 0   5 | 0   4 | 4   0 | 0   2 |
| 24 hours | 0   5 | 0   5 | 10   0 | 0   5 |
| ***After 20 turns Observed under microscope @ 250X mag. after 24 hrs. Filtered Through Screens | 0 | 0 | 0 | 0 |
| 60 Mesh | − | − | − | − |
| 100 Mesh | trace | trace | − | − |
| 250 Mesh | − | − | − | − |

TABLE V

Microscopic Observation for Crystal Growth from Selected Formulations (11)

| | *RUN No × 250 | | | | | | | | |
|---|---|---|---|---|---|---|---|---|---|
| | 18 | 19 | 20 | 21 | 22 | 23 | 24 | 25 | 26 |
| Time: | | | | | | | | | |
| 0 hrs | 0 | 0 | 0 | 0 | 0 | 0 | 0 | 0 | 0 |
| 1 hrs | 0 | 0 | 0 | 0 | 0 | 0 | 0 | 0 | 0 |
| 4 hrs | 0 | 0 | 0 | 0 | 0 | 0 | 0 | 0 | 0 |
| 24 hrs | 0 | ## | 0 | ## | 0 | 0 | 0 | 0 | 0 |
| after 24 hrs Stirring Filtered Through Screens: | | | | | | | | | |
| 60 Mesh | — | — | — | — | — | — | — | — | — |
| 100 Mesh | — | trace | — | — | — | — | — | — | — |
| 250 Mesh | — | trace | — | — | — | — | — | — | — |

EXAMPLE 4

Figure 1:
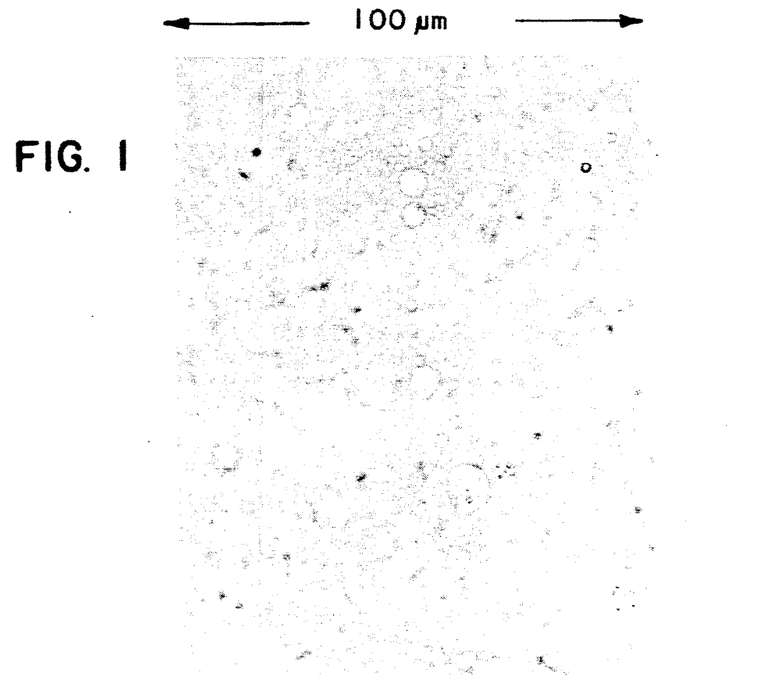
FIG. 1 is a photomicrograph of a diluted emulsion concentrate of the invention.
Figure 2:
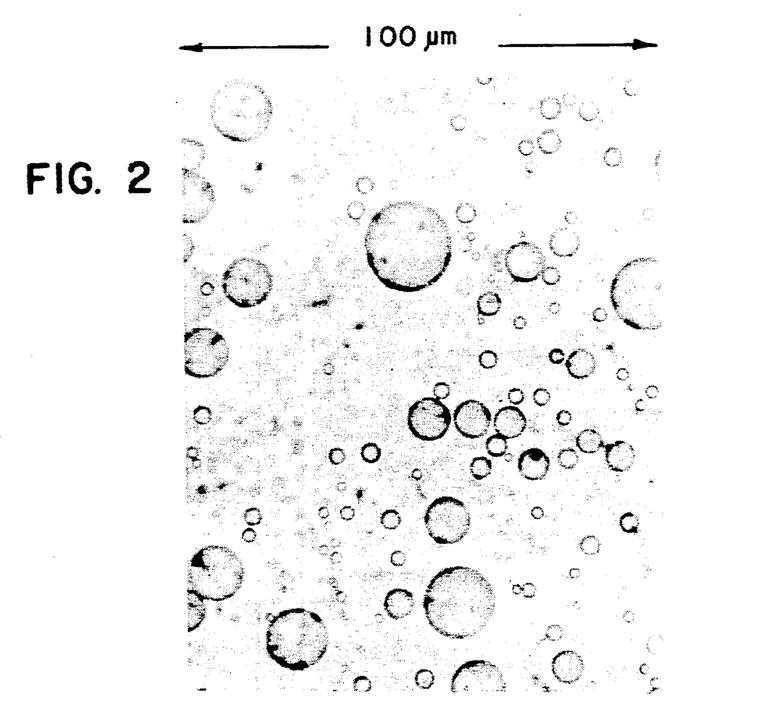
FIG. 2 is a photomicrograph of a diluted non-inventive emulsion concentrate.

Photomicrographs of diluted emulsion concentrates of 15 percent of the fungicide SXX 0665 in 342 ppm of hard water after 72 hours of stirring and under 500× magnification were taken. FIG. 1 is a photomicrograph of the diluted emulsion concentrate from Example 7 wherein dimethylamide was used to formulate the emulsion concentrate. FIG. 2 represents a photomicrograph of the emulsion obtained by the dilution of Example 26 with 342 ppm of hard water after 72 hours of stirring. As can be seen, with the present invention, significantly smaller droplets in the emulsion are achieved. This produces a finer and more uniform emulsion with increased stability.

What is claimed is:

1. A stable emulsifiable concentrate comprising an agriculturally active chemical which is substantially insoluble in water, a surfactant and a solvent selected from the group consisting of a first component of a solvent having a sufficiently high hydrophilic property and being present in an amount effective to solubilize the agriculturally active chemical, a second component having an HLB value of from about 2 to 8, and being present in an amount, in conjunction with a surfactant, effective to disperse the agriculturally active chemical, and mixtures thereof, wherein said second component comprise from about 5 to 90 percent by weight based on the total weight of the concentrate of an amide having the formula:

wherein $R^1$ is an alkyl having from 5 to 18 carbon atoms.

2. The concentrate of claim 1 wherein the Hansens' solvent factors for the first and second components are:

| Hansens' Factor | First Component | Second Component |
|---|---|---|
| dispersive | @ 56–75% | @ 56–75% |
| polarity | @ 8–24% | @ 8–24% |
| hydrogen bonding | @ 10–30% | @ 10–30%. |

3. The concentrate of claim 1 wherein the first component is selected from the group consisting of pyrrolidones having the formula wherein R is hydrogen or lower alkyl and $R_1$ is lower alkyl, cyclic lactones, lower alkyl cyclic carbonates, lower alkyl imidazolone, lower alkylamides of formic and acetic acid, and lower alkyl sulfoxides, wherein lower alkyl is an alkyl group having from 1 to 4 carbon atoms.

4. The concentrate of claim 1, wherein the second component is selected from the group consisting of pyrrolidones having the formula wherein $R_2$ is hydrogen or alkyl having from 6 to 14 carbon atoms and $R_3$ is alkyl having from 6 to 14 carbon atoms with the proviso that at least one of $R_2$ or $R_3$ must contain at least 6 carbon atoms and the sum of the carbon atoms in $R_2$ and $R_3$ cannot exceed 14;

alkyl gamma-butyrolactones, alkyl cyclic carbonates, and combinations thereof, wherein the alkyl portion may be distributed at one or more sites on the ring so long as one portion contains at least 6 carbon atoms and the total number of alkyl carbon atoms does not exceed 14.

5. The concentrate of claim 1 wherein the first component is selected from the group consisting of N-methylpyrrolidone, ethylene carbonate, propylene carbonate, butylene carbonate, N-N,dimethylimidazolone, dimethyl formamide and dimethylacetamide, dimethylsulfoxide, and mixtures thereof.

6. The concentrate of claim 1 wherein the second component is selected from the group consisting of octylpyrrolidone, dodecylpyrrolidone, N-2-ethylhexylpyrrolidone, and mixtures thereof.

7. The concentrate of claim 6 wherein the first component is N-methylpyrrolidone.

8. The concentrate of claim 1 wherein the amide is selected from the group consisting of N,N-dimethyl hexamide, N,N-dimethyl octanamide, N,N-dimethyl decanamide, N,N-dimethyl dodecanamide, N-N-dimethyl decamide, N,N-dimethyl tetradecanamide, and mixtures thereof.

9. The concentrate of claim 8 wherein the amide is a mixture of 5 weight percent N,N-dimethyl hexanamide, 50 weight percent of N,N-dimethyl octanamide, 40 weight percent N,N-dimethyl decanamide, and 5 weight percent N,N-dimethyl dodecanamide.

10. The concentrate of claim 8 wherein the amide is a mixture of 2 weight percent N,N-dimethyl decamide 95 weight percent N,N-dimetyl dodecanamide, and 3 weight percent N,N-dimethyl tetra-decanamide.

11. The concentrate of claim 1 wherein the amount of amide is from about 15 to 45 weight percent.

12. The concentrate of claim 1 which further comprises an oil having a fractional dispersive solubility parameter of greater than about 70% and a molar volume of greater than about 90 cm³/mole as an organic diluent.

13. The concentrate of claim 12 wherein the diluent is selected from the group consisting of soybean oil, rape seed oil, long chain alcohols, long chain ketones, long chain esters, and ethers, and aromatic petroleum oils.

14. The concentrate of claim 12 wherein the diluent is an aromatic petroleum oil comprising about 60% of heavy aromatic solvent naphtha and about 40% of middle distillate solvent extractant.

15. The concentrate of claim 1 wherein the agriculturally active chemical is selected from the group consisting of fertilizers, plant nutrients, plant growth accelerants, herbicides, plant growth controlling agents, insecticides, bactericides, fungicides, nematocides, defoliants, and fumigants.

16. The concentrate of claim 1 wherein the agriculturally active chemical is an herbicide selected from the group consisting of phenoxy compounds, benzoic acid, acetic acid, phthalic acid, aniline derivatives, nitriles, amides, acetamides, anilides, carbamates, thiocarbamates, heterocyclic nitrogen derivatives, urea derivatives, and phosphates.

17. The concentrate of claim 1 wherein the agriculturally active compound is a fumigant, growth regulator, repellent or rodenticide.

18. The concentrate of claim 1 wherein the agriculturally active compound is a pesticide.

19. The concentrate of claim 1 the amount of solvent is in the range from about 20 to 90%, and the amount of diluent is in the range from about 80 to 10%, each amount being based on the total weight of solvent and diluent in the concentrate.

20. The concentrate of claim 19 wherein the amount of the first component is from about 5 to 95% and the amount of the second component is from about 5 to 95% based on the weight of the concentrate.

21. The concentrate of claim 20 wherein the amount of surfactant is from about 1 to 25% by weight based on the total weight of the concentrate.

22. The concentrate of claim 21 wherein the concentration of the agriculturally active chemical is in excess of about 5 weight percent, based on the weight of the total concentrate.

23. The concentrate of claim 22 wherein the amount of the agriculturally active chemical is from about 5% to 60% by weight based on the total weight of the concentrate.

24. A composition comprising the emulsifiable concentrate of claim 1 and water wherein the agriculturally active chemical is present in an effective agriculturally active amount.

25. A method for treatment of plants comprising applying to said plant or the soil surrounding said plant the composition of claim 24.

26. A stable emulsifiable concentrate comprising an agriculturally active chemical which is substantially insoluble in water, an organic diluent, a surfactant and a solvent composed of a component having an HLB value of from about 2 to 8 and being present in an amount, in conjunction with a surfactant, effective to disperse the agriculturally active chemical and mixtures thereof, wherein said second component comprise from about 5 to 90 percent by weight based on the total weight of the concentrate of an amide having the formula:

wherein $R^1$ is an alkyl having from 5 to 18 carbon atoms.

27. The concentrate of claim 26 wherein the Hansens' solvent factors for the component is:

| Hansens' Factor | Component |
| --- | --- |
| dispersive | @ 56–75% |
| polarity | @ 8–24% |
| hydrogen bonding | @ 10–30%. |

28. The concentrate of claim 27 wherein the component is selected from the group consisting of pyrrolidones having the formula wherein
$R_2$ is hydrogen or alkyl having from 6 to 14 carbon atoms and $R_3$ is alkyl having from 6 to 14 carbon atoms with the proviso that at least one of $R_2$ or $R_3$ must contain at least 6 carbon atoms and the sum of the carbon atoms in $R_2$ and $R_3$ cannot exceed 14;
alkyl gamma-butyrolactones, alkyl cyclic carbonates, and combinations thereof, wherein the alkyl portion may be distributed at one or more sites on the ring so long as one portion contains at least 6 carbon atoms and the total number of alkyl carbon atoms does not exceed 14.

29. The concentrate of claim 27 wherein the component is selected from the group consisting of octylpyrrolidone, dodecylpyrrolidone, N-(2'-ethylhexylpyrrolidone), and mixtures thereof.

30. The concentrate of claim 27 wherein the amide is selected from the group consisting of N,N-dimethyl hexamide, N,N-dimethyl octanamide, N,N-dimethyl decanamide, N,N-dimethyl dodecanamide, N-N-dimethyl decamide, N,N-dimethyl tetradecanamide, and mixtures thereof.

31. The concentrate of claim 27 wherein the amide is a mixture of 5 weight percent N,N-dimethyl hexamide, 50 weight percent of N,N-dimethyl octanamide 40 weight percent N,N-dimethyl decanamide, and 5 weight percent N,N-dimethyl dodecanamide.

32. The concentrate of claim 30 wherein the amide is a mixture of 2 percent N,N-dinetyl decamide 95 percent N,N-dimetyl dodecanamide, and 3 percent N,N-dimethyl tetra-decanamide.

33. The concentrate of claim 26 wherein the amount of amide is from about 15 to 45 weight percent.

34. The concentrate of claim 26 which further comprises an oil having a fractional dispersive solubility parameter of a greater than about 70% and a molar volume of greater than about 90 cm³/mole.

35. The concentrate of claim 34 wherein the diluent is selected from the group consisting of soybean oil, rape seed oil, long chain alcohols, long chain ketones, long chain esters, and ethers, and aromatic petroleum oils.

36. The concentrate of claim 35 wherein the diluent is an aromatic petroleum oil comprising about 60% of heavy aromatic solvent naphtha and about 40% of middle distillate solvent extractant.

37. The concentrate of claim 26 wherein the agriculturally active chemical is selected from the group consisting of fertilizers, plant nutrients, plant growth accelerants, herbicides, plant growth controlling agents, insecticide,, bactericides, fungicides, nematocides, defoliants, and fumigants.

38. The concentrate of claim 26 wherein the agriculturally active chemical is an herbicide selected from the group consisting of phenoxy compounds, benzoic acid, acetic acid, phthalic acid, aniline derivatives, nitriles, amides, acetamides, anilides, carbamates, thiocarbamates, heterocyclic nitrogen derivatives, urea derivatives, and phosphates.

39. The concentrate of claim 26 wherein the agriculturally active compound is a fumigant, growth regulator, repellent or rodenticide.

40. The concentrate of claim 26 wherein the agriculturally active compound is a pesticide.

41. The concentrate of claim 26 the amount of solvent is in the range from about 20 to 90%, and the amount of diluent is in the range from about 80 to 10%, each amount being based on the total weight of solvent and diluent in the concentrate.

42. The concentrate of claim 26 wherein the amount of surfactant is from about 1 to 25% by weight based on the total weight of the concentrate.

43. The concentrate of claim 42 wherein the concentration of the agriculturally active chemical is in excess of about 5 weight percent, based on the weight of the total concentrate.

44. The concentrate of claim 43 wherein the amount of the agriculturally active chemical is from about 5% to 25% by weight based on the total weight of the concentrate.

45. A composition comprising the emulsifiable concentrate of claim 26 and water wherein the agriculturally active chemical is present in an effective agriculturally active amount.

46. The composition of claim 45 wherein the concentration of the active chemical is in the range from about 10 ppm to 2 percent by weight.

47. A method for treatment of plants comprising applying to said plant or the soil surrounding said plant the composition of claim 45.

* * * * *

UNITED STATES PATENT AND TRADEMARK OFFICE
CERTIFICATE OF CORRECTION

PATENT NO. : 5,283,229
DATED : February 1, 1994
INVENTOR(S) : Kolazi S. Narayanan, et al It is certified that error appears in the above-indentified patent and that said Letters Patent is hereby corrected as shown below:

Column 2, lines 17-19, change "Patent Applications Serial No. 448,707, filed December 11, 1989, Serial No. 505,030, filed April 5, 1990, and Serial No. 546,014, filed June 28, 1990" to -- Patents No. 5,071,463, 5,160,528, and 5,156,666 --

Column 2, line 24, change "56 to 75%" to -- 40 to 50% --;

Column 2, line 25, change "8 to 24%" to -- 25 to 40% --;

UNITED STATES PATENT AND TRADEMARK OFFICE
CERTIFICATE OF CORRECTION

PATENT NO. : 5,283,229
DATED : February 1, 1994
INVENTOR(S) : Kolazi S. Narayanan, et al It is certified that error appears in the above-indentified patent and that said Letters Patent is hereby corrected as shown below:

Column 2, before line 27, insert the following paragraph:
-- The second component is a hydrophobic solvent having the following Hansens' solvent parameters:
Dispersable component of from about 56 to 75%;
Polar component of from about 8 to 24%;
H-bonding component of from about 10 to 30%. --

IN THE CLAIMS
Column 19, Claim 2, in the table,
line 2, change "56-75%" first occurrence to -- 40-50% --;
line 3, change " 8-24%" first occurrence to -- 25-40% --.

Signed and Sealed this

Fourteenth Day of June, 1994

*Attest:*

BRUCE LEHMAN

*Attesting Officer*      *Commissioner of Patents and Trademarks*